US012799214B2

(12) United States Patent
Ginsberg et al.

(10) Patent No.: US 12,799,214 B2
(45) Date of Patent: Nov. 17, 2026

(54) IMMUNOMODULATORY COMPOUNDS

(71) Applicant: The Regents of the University of California, Oakland, CA (US)

(72) Inventors: Mark Ginsberg, LaJolla, CA (US); Hao Sun, La Jolla, CA (US); Jailal Ablack, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1130 days.

(21) Appl. No.: 17/633,912

(22) PCT Filed: Aug. 10, 2020

(86) PCT No.: PCT/US2020/045568

§ 371 (c)(1),
(2) Date: Feb. 8, 2022

(87) PCT Pub. No.: WO2021/030241

PCT Pub. Date: Feb. 18, 2021

(65) Prior Publication Data

US 2022/0289855 A1 Sep. 15, 2022

Related U.S. Application Data

(60) Provisional application No. 62/884,699, filed on Aug. 9, 2019.

(51) Int. Cl.
*C07K 16/28* (2006.01)
*A61P 37/02* (2006.01)

(52) U.S. Cl.
CPC .......... *C07K 16/2866* (2013.01); *A61P 37/02* (2018.01); *C07K 2317/524* (2013.01); *C07K 2317/55* (2013.01); *C07K 2317/71* (2013.01)

(58) Field of Classification Search
None
See application file for complete search history.

(56) References Cited

U.S. PATENT DOCUMENTS

2014/0302028 A1 10/2014 Zha

FOREIGN PATENT DOCUMENTS

WO 2018167194 A1 9/2018

OTHER PUBLICATIONS

Arce Vargas et al. 'Fc-Optimized Anti-CD25 Depletes Tumor-Infiltrating Regulatory T Cells and Synergizes with PD-1 Blockade to Eradicate Established Tumors.' Arce Vargas et al., 2017, Immunity 46, 577-586 Apr. 18, 2017 http://dx.doi.org/10.1016/j.immuni.2017.03.013.*

Shields et al. 'High Resolution Mapping of the Binding Site on Human IgG1 for FcgRI, FcgRII, FcgRIII, and FcRn and Design of IgG1 Variants with Improved Binding to the FcgR*.' J. Bio. Chem. 276(9:6591-6604, 2001.*

Sailer et al. 'Molecular ensembles make evolution unpredictable.' PNAS 114(45):11938-11943, 2017.*

Sun et al. 'IL-2 can signal via chemokine receptors to promote regulatory T cells' suppressive function.' Sun et al., 2023, Cell Reports 42, 112996 https://doi.org/10.1016/j.celrep.2023.112996.*

Goel et al. Plasticity within the Antigen-Combining Site May Manifest as Molecular Mimicry in the Humoral Immune Response. 1 J. Immunol. 173(12)7358-7367, 2004.*

Kahn et al. 'Adjustable Locks and Flexible Keys: Plasticity of Epitope-Paratope Interactions in Germline Antibodies.' J. Immunol. 192:5398-5405, 2014.*

Poosarla et al. 'Computational De Novo Design of Antibodies Binding to a Peptide With High Affinity.' Biotech. Bioeng. 114(6): 1331-1342, 2017.*

Huss et al. 'Anti-CD25 monoclonal antibody Fc variants differentially impact regulatory T cells and immune homeostasis.' Immunology, 148, 276-286, 2016.*

Baudino et al. 'Crucial Role of Aspartic Acid at Position 265 in the CH2 Domain for Murine IgG2a and IgG2b Fc-Associated Effector Functions.' The Journal of Immunology, 2008, 181: 6664-6669.*

Pfender et al. 'Daclizumab (anti-CD25) in multiple sclerosis.' Experimental Neurology 262 (2014) 44-51.*

PCT International Search Report and Written Opinion for PCT/US2020/045568 mailed Mar. 12, 2021 (6 pages).

Boyman et al. "The role of interleukin-2 during homeostasis and activation of the immune system," Nat Rev Immunol, Feb. 17, 2012, vol. 12, pp. 180-190.

Clynes et al. "Inhibitory Fc receptors modulate in vivo cytoxicity against tumor agents," Nature Medicine, Apr. 1, 2000, vol. 6, pp. 443-446.

Huss et al. "Anti-CD25 monoclonal antibody Fc variants differentially impact regulatory T cells and immune homeostasis," Immunology, May 12, 2016, vol. 148, pp. 276-286.

(Continued)

*Primary Examiner* — Nora M Rooney
(74) *Attorney, Agent, or Firm* — Meunier Carlin & Curfman LLC

(57) ABSTRACT

Antibodies against CD25 engineered with dysfunctional constant regions used to bind T regulatory cells to activate integrin to inhibit immune responses and for treatment of autoimmune diseases such as systemic lupus erythematosus, multiple sclerosis, rheumatoid arthritis, and inflammatory bowel disease, in addition to transplantation rejection. The invention demonstrates that treatment of CD4+ T cells with CD25 antibody results in rapid activation of multiple integrins as measured by soluble ligand binding.

4 Claims, 5 Drawing Sheets

Specification includes a Sequence Listing.

(56) References Cited

OTHER PUBLICATIONS

Rech et al., "CD25 blockade depletes and selectively reprograms regulatory T cells in concert with immunotherapy in cancer patients", Sci. Transl. Med., 4(134), 134ra62 (May 16, 2012).
Sun et al., "IL-2 can signal via chemokine receptors to promote regulatory T cells' suppressive function", Cell Reports, 42, 112996 (Aug. 29, 2023).
Stephens et al. "CD4+CD25+ regulatory T cells limit the risk of autoimmune disease arising from T cell receptor crossreactivity", Proc. Natl. Acad. Sci. USA, 102, 17418-17423 (Nov. 29, 2005).

* cited by examiner

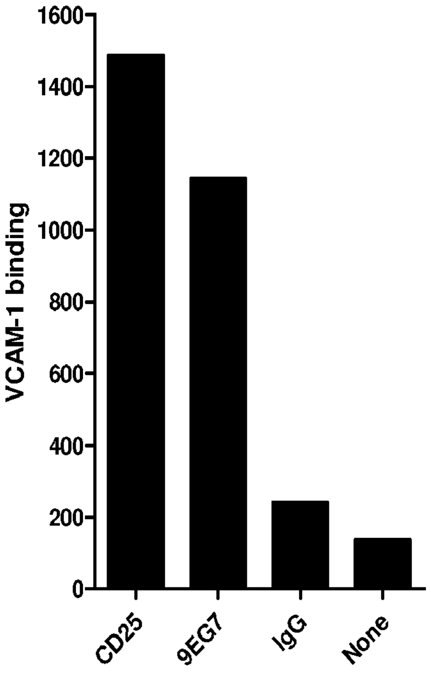
FIG. 1
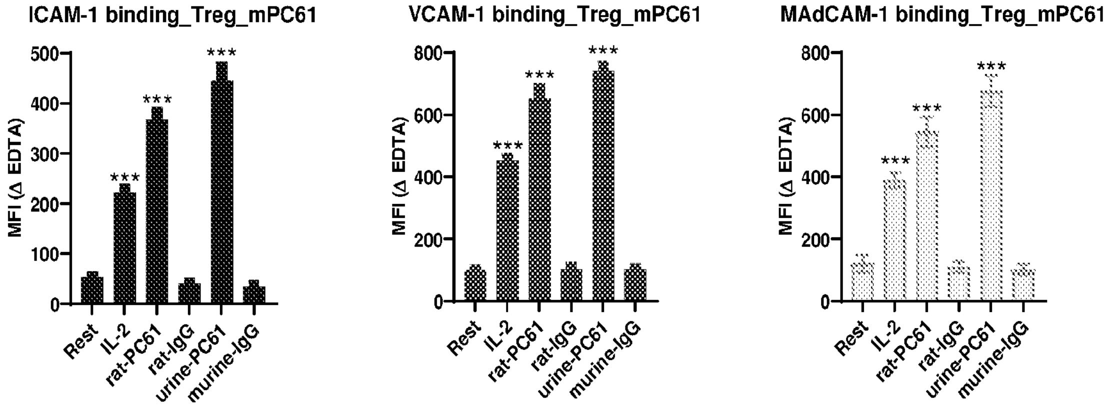
FIG. 2A
FIG. 2B
FIG. 2C

SEQUENCE LISTING

```
<160> NUMBER OF SEQ ID NOS: 8

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Ser Gly Ala Glu Leu Val Arg Pro Gly Thr
1               5                   10                  15

Ser Val Lys Leu Ser Cys Lys Val Ser Gly Asp Thr Ile Thr Ala Tyr
            20                  25                  30

Tyr Ile His Phe Val Lys Gln Arg Pro Gly Gln Gly Leu Glu Trp Ile
        35                  40                  45

Gly Arg Ile Asp Pro Glu Asp Asp Ser Thr Glu Tyr Ala Glu Lys Phe
    50                  55                  60

Lys Asn Lys Ala Thr Ile Thr Ala Asn Thr Ser Ser Asn Thr Ala His
65                  70                  75                  80

Leu Lys Tyr Ser Arg Leu Thr Ser Glu Asp Thr Ala Thr Tyr Phe Cys
                85                  90                  95

Thr Thr Asp Asn Met Gly Ala Thr Glu Phe Val Tyr Trp Gly Gln Gly
```

```
            100                 105                 110

Thr Leu Val Thr Val Ser Ser
        115


<210> SEQ ID NO 2
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Val Leu Thr Gln Pro Lys Ser Val Ser Ala Ser Leu Glu Ser
1               5                   10                  15

Thr Val Lys Leu Ser Cys Lys Leu Asn Ser Gly Asn Ile Gly Ser Tyr
            20                  25                  30

Tyr Met His Trp Tyr Gln Gln Arg Glu Gly Arg Ser Pro Thr Asn Leu
        35                  40                  45

Ile Tyr Arg Asp Asp Lys Arg Pro Asp Gly Ala Pro Asp Arg Phe Ser
    50                  55                  60

Gly Ser Ile Asp Ile Ser Ser Asn Ser Ala Phe Leu Thr Ile Asn Asn
65                  70                  75                  80

Val Gln Thr Glu Asp Glu Ala Met Tyr Phe Cys His Ser Tyr Asp Gly
                85                  90                  95

Arg Met Tyr Ile Phe Gly Gly Gly Thr Lys Leu Thr Val Leu Gly Gln
            100                 105                 110

Pro


<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Tyr Tyr Ile His
1               5


<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ile Asp Pro Glu Asp Asp Ser Thr Glu Tyr Ala Glu Lys Phe Lys
1               5                   10                  15


<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Cys Thr Thr Asp Asn Met Gly
```

```
1               5


<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Asn Ser Gly Asn Ile Gly Ser Tyr Tyr Met
1               5                   10


<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Arg Asp Asp Lys Arg Pro
1               5


<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Phe Cys His Ser Tyr Asp Gly Arg
1               5
```

IMMUNOMODULATORY COMPOUNDS

CROSS REFERENCE TO RELATED APPLICATIONS

This application claims the priority benefit of PCT/US2020/045568, filed Aug. 10, 2020, which claims the priority benefit to U.S. Provisional Patent Application No. 62/884,699, filed Aug. 9, 2019, the entire contents of which applications are incorporated herein by reference.

GOVERNMENT SUPPORT

The invention was made with government support under Grant No. HL078784 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 22, 2025, is named 24978-0700_SL and is 3,974 bytes in size.

TECHNICAL FIELD

The present invention relates to new immunomodulatory compounds.

BACKGROUND

Regulatory T cells (Treg) play a critical role in controlling immune responses, chronic inflammation and autoimmune disease. Integrin activation in $CD4^+$ $FoxP3^+$ Tregs is crucial to the maintenance of Treg numbers and function in vivo (Klann et al., 2017, 2018). Tregs also express high levels of the low affinity IL-2 receptor CD25 (IL-2Ra, TAC) on their cell surface. Thus, one mechanism by which Tregs are thought to limit immune responses is by sequestering the available IL-2, effectively starving effectors and leading to peripheral tolerance. Importantly, CD25 antibodies can deplete Tregs in vivo (Setiady et al., 2010). Thus, treatment with such antibodies would be expected to exacerbate autoimmunity. Published work indicates that this depletion depends on the capacity of Fc receptor bearing cells to recognize the bound anti-CD25, thereby phagocytizing and destroying the Tregs (Setiady et al., 2010).

SUMMARY OF THE INVENTION

The invention demonstrates that treatment of $CD4^+$ T cells with CD25 antibody results in rapid activation of multiple integrins as measured by soluble ligand binding.

The invention provides antibodies targeting CD25 and engineered with Fc domains that are not productively recognized by Fc receptors, which do not inhibit or do not block IL-2 from binding to CD25. The invention provides antibodies targeting CD25 that stimulate integrin activation and $\alpha L\beta 2$, $\alpha 4\beta 1$, and $\alpha 4\beta 7$ in $CD4^+$ $Foxp3^+$ T-regulatory cells. The invention provides antibodies targeting CD25 that can be used to promote Treg immunosuppressive function in vitro and in vivo. Such engineered anti-CD25 antibodies and CD25 binding fragments thereof can be used to suppress immune responses for example for the treatment of autoimmune diseases such as systemic lupus erythematosus or inflammatory bowel disease, or in the context of alleviating organ transplantation rejection, e.g., pancreatic islet transplantation. The antibodies may be used for reducing organ transplantation rejection for any transplantation surgeries, including for the heart, kidney, liver, lung, intestine, cornea, bone marrow, connective tissue, and vascularized composite allografts.

The invention also provides for the use of effective CD25 binding agents, such as antibodies, polymers of single-chain variable fragments (scFv), multivalent non-antibody CD25 ligands, and aptamers targeting CD25 binding, which do not inhibit or do not block IL-2 from binding to CD25. The invention provides methods of identifying such effective CD25 binding agents.

BRIEF DESCRIPTION OF THE DRAWINGS

FIG. 1 shows VCAM binding determined by flow cytometry.

FIGS. 2A-2C show engineered murine anti-CD25 (murine-PC61) activates integrins $\alpha L\beta 2$, $\alpha 4\beta 1$, and $\alpha 4\beta 7$ in $CD4^+$ $Foxp3^+$ T-regulatory cells determined by flow cytometry.

DETAILED DESCRIPTION

Figure 3:
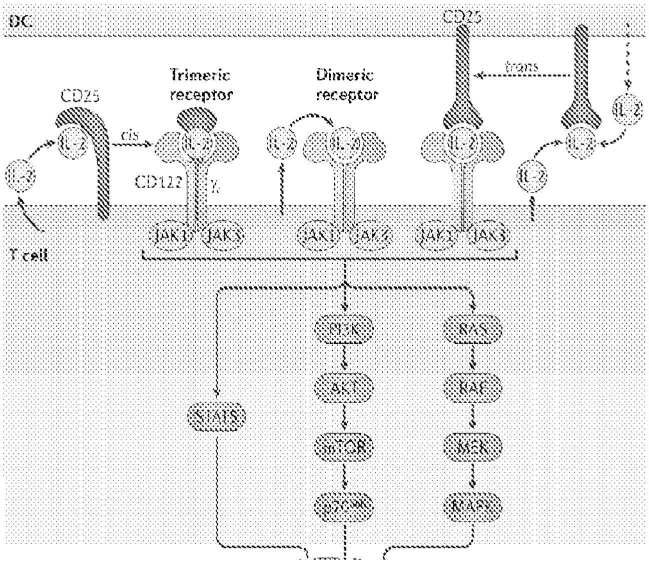
FIG. 3 shows that phosphorylation of STAT 5 is a readout of "canonical" IL-2 signaling.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, 20th ed., (Lippincott, Williams & Wilkins 2003), and Remington, The Science and Practice of Pharmacy, 22th ed., (Pharmaceutical Press and Philadelphia College of Pharmacy at University of the Sciences 2012).

In embodiments, the invention provides an anti-CD25 antibody comprising a Fab region that specifically binds to CD25 on T lymphocytes, and a mutated Fc region that does not bind to a Fc receptor.

In embodiments, the invention provides that the antibody does not block IL-2 binding to CD25. In embodiments the antibody increases regulatory T cell (Tregs) immunosuppressive function. In embodiments, the antibody does not deplete regulatory T cells in vivo. In embodiments, the antibody induces activation of integrins αLβ2, α4β1, and α4β7 in $CD4^+$ $Foxp3^+$ T-regulatory cells.

In embodiments, the invention provides an anti-CD25 antibody comprising a mutated Fc region that is mutated as compared to a naturally occurring constant region such that Fc receptor bearing cells do not recognize the bound anti-CD25, thereby inhibiting phagocytosis of Tregs. In embodiments, the Fc region is truncated with one or more deletion mutations, contains one or more substitution mutations, and/or contains one or more insertion mutations, as compared to a naturally occurring Fc region.

In embodiments, the invention provides a CD25 binding agent that has an ability to bind to CD25 without inhibiting IL-2 binding to CD25. In embodiments, the CD25 binding agent increases regulatory T cell (Tregs) immunosuppressive function. In embodiments, the CD25 binding agent does not deplete regulatory T cells in vivo. In embodiments, the CD25 binding agent induces activation of integrins αLβ2, α4β1, and α4β7 in $CD4^+$ $Foxp3^+$ T-regulatory cells.

In embodiments, the invention provides methods of treating an autoimmune disease or transplant rejection in a subject comprising administering to a subject in need an effective amount of the anti-CD25 antibody or CD25 binding agent of any of the embodiments disclosed herein. In embodiments, the autoimmune disease is systemic lupus erythematosus, multiple sclerosis, rheumatoid arthritis, chronic inflammation, or inflammatory bowel disease. In embodiments, the transplant rejection is due to pancreatic islet, heart, kidney, liver, lung, intestine, cornea, bone marrow, or connective tissue, transplantation or vascularized composite allografts.

In embodiments, the invention provides methods of inhibiting an immune response in a subject comprising administering to a subject in need an effective amount of the anti-CD25 antibody or CD25 binding agent of any of the embodiments disclosed herein.

In embodiments, the invention provides methods of stimulating regulatory T cells (Tregs) in a subject, comprising administering to a subject in need an effective amount of the anti-CD25 antibody or CD25 binding agent of any of the embodiments disclosed herein.

In embodiments, the invention provides pharmaceutical compositions comprising the anti-CD25 antibody or CD25 binding agent of any of the embodiments disclosed herein and a pharmaceutically acceptable excipient.

In embodiments, the invention provides a method of identifying a binding agent of interest, comprising screening a candidate agent for an ability to bind to CD25 without inhibiting IL-2 binding. In embodiments, the CD25 binding agent of interest has a mutated or truncated Fc region.

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a fusion protein, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

It is understood that aspects and embodiments of the invention described herein include "consisting" and/or "consisting essentially of" aspects and embodiments.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated.

As used herein the term "pharmaceutical composition" refers to a pharmaceutical acceptable compositions, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

The term "antibody" as used herein encompasses monoclonal antibodies (including full length monoclonal antibodies), polyclonal antibodies, multi-specific antibodies (e.g., bi-specific antibodies), and antibody fragments so long as they exhibit the desired biological activity of binding to a target antigenic site and its isoforms of interest. The term "antibody fragments" comprise a portion of a full length antibody, generally the antigen binding or variable region thereof including the CDRs specific for CD25 binding. Antibodies of the invention can have a Fc region (heavy chain constant domains) that is not productively recognized or does not effectively bind to a Fc receptor or other immune molecules, to elicit an immune response normally produced by a native Fc region, such as macrophage phagocytosis. Such antibodies can be routinely engineered including by amino acid sequence truncation, deletion, insertion, or substitution mutations or by binding the Fc region with a masking agent. In general, antibody molecules may relate to any of the classes IgG, IgM, IgA, IgE and IgD, which differ from one another by the nature of the heavy chain present in the molecule. Certain classes have subclasses as well, such as $IgG_1$, $IgG_2$, and others.

The term "antibody" as used herein encompasses any antibodies derived from any species and resources, including but not limited to, human antibody, rat antibody, mouse antibody, rabbit antibody, and so on, and can be synthetically made or naturally-occurring.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The "monoclonal antibodies" may also be isolated from phage antibody libraries using the techniques known in the art.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-polyacrylamide gel electrophoresis under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

In order to avoid potential immunogenicity of the monoclonal antibodies in humans, the monoclonal antibodies that have the desired function are preferably human or humanized "Humanized" forms of non-human (e.g., murine) antibodies are chimeric antibodies that contain minimal sequence derived from non-human immunoglobulin. For the most part, humanized antibodies are human immunoglobulins (recipient antibody) in which hyper variable region residues of the recipient are replaced by hyper variable region residues from a non-human species (donor antibody) such as mouse, rat, rabbit or nonhuman primate having the desired specificity, affinity, and capacity. Furthermore, humanized antibodies may comprise residues that are not found in the recipient antibody or in the donor antibody. These modifications are made to further refine antibody performance.

Table 1 shows exemplary embodiments of the Heavy and Light chain variable region amino acid sequence of an exemplary anti-CD25 rat antibody obtained from PC61.5.3. The three CDRs in each variable region are bolded. Sequences are derived from Huss, D. J. et al. *Immunology* 148, 276-86 (2016).

TABLE 1

| Chain | Sequence |
|---|---|
| Heavy | QVQLQQSGAELVRPGTSVKLSCKVSGDTIT**AYYIH**FVKQRPGQGLEWIG**RIDPEDDSTEYAEKFK**NKATITANTSSNTAHLKYSRLTSEDTATY**FCTTDNMG**ATEFVYWGQGTLVTVSS (SEQ ID NO: 1) |
| Light | QVVLTQPKSVSASLESTVKLSCK**LNSGNIGSYYM**HWYQQREGRSPTNLI**YRDDKRP**DGAPDRFSGSIDISSNSAFLTINNVQTEDEAM**YFCHSYDGR**MYIFGGGTKLTVLGQP (SEQ ID NO: 2) |

Table 2 shows the CDR sequences of exemplary antibodies of the present invention.

TABLE 2

| |
|---|
| VH CDR1: AYYIH (SEQ ID NO: 3) |
| VH CDR2: RIDPEDDSTEYAEKFK (SEQ ID NO: 4) |
| VH CDR3: FCTTDNMG (SEQ ID NO: 5) |
| VL CDR1: LNSGNIGSYYM (SEQ ID NO: 6) |
| VL CDR2: YRDDKRP (SEQ ID NO: 7) |
| VL CDR3: YFCHSYDGR(SEQ ID NO: 8) |

The present invention provides anti-CD25 antibodies having at least 50%, 60%, 70%, 75%, 80%, 85%, 90%, 91%, 92%, 93%, 94%, 95%, 96%, 97%, 98% or 99% identity to each heavy or light chain variable region, or to the individual CDRs, as disclosed in any of SEQ ID NOs: 1-8. For example, the present invention provides anti-CD25 antibodies that specifically bind to CD25, that increase Tregs suppressive function, induce activation of integrins αLβ2, α4β1, and α4β7, and/or do not inhibit IL-2 binding or cause Tregs depletion in vivo, comprising: a) a heavy chain variable (VH) region at least 90% identical to a VH region of SEQ ID NO:1 or VH CRDs 1-3 as shown in SEQ ID NOs: 3-5; and b) a light chain variable (VL) region at least 90% identical to a VL region of SEQ ID NO:2 or VL CRDs 1-3 as shown in SEQ ID NOs: 6-8.

Two anti-human CD25 antibodies, Basiliximab and Daclizumab, that do inhibit IL-2 binding are commercially available. Basiliximab is used to prevent rejection in organ transplantation. The antibodies of the present invention inhibit IL-2 biding to a lesser extent than Basiliximab and Daclizumab. When compared with prior antibodies, the anti-CD25 antibodies of the present invention increase Tregs' suppressive function, induce activation of integrins αLβ2, α4β1, and α4β7, but do not inhibit IL-2 binding or cause Tregs depletion in vivo. Modification of the VH and VL regions of available antibodies and screening for the desired activity is well-known.

It is understood that any class of antibodies, or fragments thereof, may be used, such as IgG, IgM, IgA, IgE and IgD. Moreover, fusion proteins, such as a single-chain variable fragment (scFv), which targets CD25 but lacks an effector functioning Fc region may also be employed. It is further understood that any truncation or mutation of the Fc domain to inhibit recognition by the Fc receptors can be used. There are many well-known ways to reduce the Fc effector function. For example, to avoid mouse IgG1 binding to mouse Fc receptors, D265 may be mutated to Ala (Bournazos et al., 2014; Clynes et al., 2000).

Other methods for modifying FC domains against receptor recognition are described in Kang and Jung, *Experimental & Molecular Medicine* (2019). For example, the N-linked glycan may be removed by mutating N297 with other residues. Further, the residues responsible for FcγRs or C1q binding may be mutated. Moving the Fab region to other IgG subclasses, such as IgG2 or IgG4, which engages less tightly to FcγRs is another option. More than one method may be used.

EXAMPLES

Example 1: $CD4^+$ T cells were isolated from the spleen of wt C57B16 mice. $CD4^+$ T cells were incubated with indicated treatments (antibodies at 1 μg/ml, EDTA at 5 Mm) and 10 μg/ml purified mouse VCAM-Fc at 37 °C+5% $CO_2$. After 30 minutes, cells were washed with cold HBSS and stained with 10 μg/ml of anti-Human Fc-PE conjugate for 30 minutes on ice. Cells were washed twice and soluble VCAM binding was determined by Flow cytometry. Nonspecific VCAM1-Binding for each condition was subtracted using EDTA treated controls. Results are shown in FIG. 1.

Example 2: Murine anti-CD25 regulates integrin activation on leukocytes. Integrin activation was tested by measuring their ligand binding ability (FIGS. 2A-2C). Addition of IL-2 stimulated the binding of soluble ICAM-1, VCAM-1, and MAdCAM-1 to Regulatory T cells (Tregs), indicating that IL-2 induces the activation of integrins αLβ2, α4β1, and α4β7 on Tregs. Rat-PC61, a commercial antibody that binds to mouse CD25, but does not block IL-2 binding, promoted Tregs binding to all the three ligands compared with rat IgG control. An anti-CD25 antibody that blocks IL-2 binding (3C7) did not activate integrins (data not shown). Since injection of rat-PC61 into the mouse depleted Tregs mediated by $Fc\gamma RIII^+$ phagocytes (Setiady et al., 2010), the murine-PC61 was engineered so that the Fc region was from mouse IgG1. To avoid mouse IgG1 binding to mouse Fc receptors, D265 was mutated to Ala (Bournazos et al., 2014; Clynes et al., 2000). Consistent with the rat-PC61, the murine-PC61 could also stimulate the activation of integrins αLβ2, α4β1, and α4β7 on Tregs.

Specifically, FIGS. 2A-2C show binding of soluble ICAM-1, VCAM-1 or MAdCAM-1 (10 ug/ml) to YFP+ Tregs isolated from Foxp3GFP mice in the presence of IL-2 (10 ug/ml), rat-PC61 (5 ug/ml), rat-rIgG (5 ug/ml), murine-PC61 (5 ug/ml) and murine-IgG (5 ug/ml). Data represent mean±SEM. Two-tailed t-test. ***P<0.001.

Splenic lymphocytes were isolated from $Foxp3^{GFP}$ mice and were washed and resuspended in HBSS containing 0.1% BSA and 1 mM $Ca^{2+}/Mg^{2+}$, prior to incubation with integrin ligands for 30 mM at 37 °C in the presence of IL-2 (10 ug/ml), rat-PC61 (5 ug/ml, Bioxcell), rat-rIgG (5 ug/ml, Bioxcell), murine-PC61 (5 ug/ml) and murine-IgG (5 ug/ml, Bioxcell). Cells were then incubated with AlexFluor647-conjugated anti-human IgG (1:200) for 30 mM at 4 °C. Then cells were washed twice before flow cytometry analysis using an Accuri C6 Plus (BD Biosciences). Data were analyzed using FlowJo software.

Example 3: Phosphorylation of STAT 5 is a Readout of "Canonical" IL-2 Signaling, as shown by FIG. 3. Interleukin-2 (IL-2), a 15 kDa four-α-helix bundle cytokine, is secreted as a soluble molecule by activated T cells and to a lesser extent by activated dendritic cells (DCs). IL-2 can bind to the IL-2 receptor (IL-2R) subunit CD25 (also known as IL-2Ra) with a dissociation constant (Kd) of ~10-8M, and this interaction induces a distinct conformational change in IL-2 that increases its affinity for the IL-2R subunit CD122 (also known as IL-2Rβ). Subsequently, the IL-2-CD25 dimer recruits CD122 followed by the common cytokine receptor γ-chain (γc), another subunit of the IL-2R. This quaternary IL-2IL-2R complex has a Kd of ~10-11 M. In cells that lack expression of CD25, IL-2 can associate with the dimeric IL-2R directly (with a Kd of ~10-9M). Alternatively, T cell- or DC-derived IL-2 can bind to CD25 molecules expressed by DCs, and this IL-2 can then be presented in trans to neighboring T cells that express CD122 and γc. On binding to CD122 and γc, IL-2 induces the transcription of target genes (such as Cd25) through several signalling pathways, including the Janus kinase (JAK)-signal transducer and activator of transcription (STATS) pathway, the phosphoinositide 3-kinase (PI3K)-AKT pathway and the mitogen-activated protein kinase (MAPK) pathway. MEK, MAPK/ERK kinase; mTOR, mammalian target of rapamycin; p70S6K, p70 S6 kinase (Boyman and Sprent, 2012).

Figure 4A:
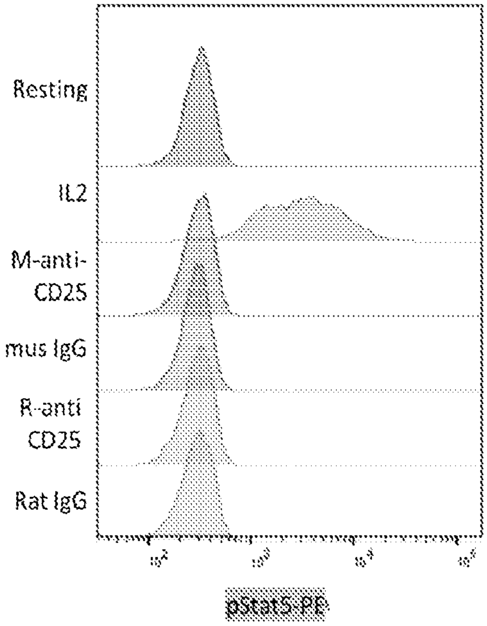
FIGS. 4A-4B show that the anti-CD25 antibody PC61 mediated signals transmission is independent of canonical IL-2 signaling pathway.
Figure 4B:
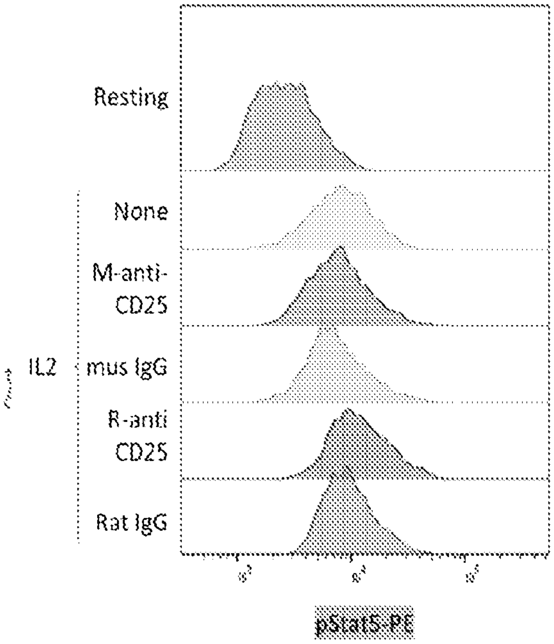

Example 4: To investigate whether the anti-CD25 antibody PC61 transmits signals thorough the classic IL-2 signaling pathway, the phosphorylation of Stat5 on Tregs was tested after PC61 stimulation. IL-2 stimulation induced significant phosphorylation of Stat5. However, neither rat-PC61 nor murine-PC61 induced phosphorylation of Stat5 (FIG. 4A). The results indicate the anti-CD25 antibody PC61 mediated signals transmission is independent of canonical IL-2 signaling pathway. It was unclear whether the anti-CD25 antibody PC61 blocks the canonical IL-2 signaling pathway. Thus, the cells were stimulated with IL-2 together with PC61, and then the phosphorylation level of Stat5 were measured. Both rat-PC61 and murine-PC61 did not affect IL-2-induced Stat5 phosphorylation (FIG. 4B).

Specifically, FIG. 4A shows the phosphorylation level of Stat5 on Tregs isolated from C57BL/6J mice in the presence of IL-2 (10 ug/ml), rat-PC61 (5 ug/ml), rat-rIgG (5 ug/ml), murine-PC61 (5 ug/ml) or murine-IgG (5 ug/ml). FIG. 4B shows the phosphorylation level of Stat5 on Tregs isolated from C57BUJ mice in the presence of IL-2 (10 ug/ml) plus rat-PC61 (5 ug/ml), rat-rIgG (5 ug/ml), murine-PC61 (5 ug/ml) or murine-IgG (5 ug/ml).

Splenic lymphocytes isolated from C57BL/6J mice were treated with IL-2 (10 ug/ml), rat-PC61 (5 ug/ml, Bioxcell), rat-rIgG (5 ug/ml, Bioxcell), murine-PC61 (5 ug/ml) and murine-IgG (5 ug/ml, Bioxcell) for 30 min at 37 °C, fixed and permeabilized with the Foxp3 transcription factor fixation/permeabilization kit (eBioscience) prior to PE-conjugated pStatS and AlexFluor647-conjugated Foxp3 staining. Then the cells were washed twice before flow cytometry analysis using an Accuri C6 Plus (BD Biosciences). Data were analyzed using FlowJo software.

Example 5: To further confirm that the anti-CD25 antibody PC61 mediated signals transmission is independent on the canonical IL-2 signaling pathway, PC61-induced integrin activation on Tregs was tested while blocking IL-2Rβ, with an antibody used to inhibit IL-2 signaling (Ku et al., 2000). IL-2Rβ blocking antibody treatment suppressed IL-2-stimulated integrin activation on Tregs, but not PMA or rat-PC61. Those results show that PC61 mediated signaling is independent on the canonical IL-2 signaling pathway.

Figure 5:
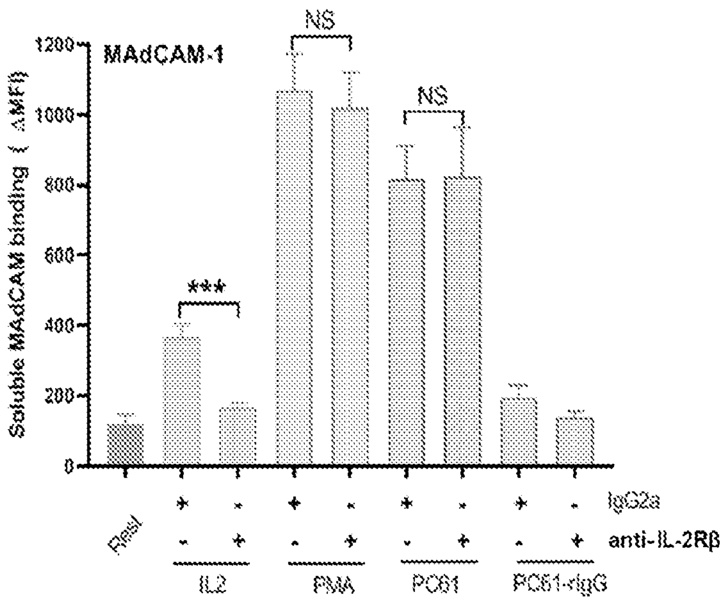
FIG. 5 shows PC61-induced integrin activation on Tregs while blocking IL-2R$\beta$ with an antibody used to inhibit canonical IL-2 signaling.

Specifically, FIG. 5 shows binding of soluble MAdCAM-1 to YFP+ Tregs isolated from Foxp3GFP mice in the presence of IL-2 (10 ug/ml), PMA (100 nM), rat-PC61 (5 ug/ml) and rat-rIgG (5 ug/ml) with or without IL-2Rβ blocking antibody (TM-β1). Data represent mean±SEM. Two-tailed t-test. ***P<0.001.

Splenic lymphocytes isolated from Foxp3$^{GFP}$ mice were washed and resuspended in HBSS containing 0.1% BSA and 1 mM $Ca^{2+}/Mg^{2+}$, prior to incubation with MAdCAM-1 (10 ug/ml) for 30 min at 37 °C in the presence of IL-2 (10 ug/ml), PMA (100 nM), rat-PC61 (5 ug/ml, Bioxcell) and rat-rIgG (5 ug/ml, Bioxcell) with or without IL-2Rβ blocking antibody (TM-β1, biolegend). Cells were then incubated with AlexFluor647-conjugated anti-human IgG (1:200) for 30 min at 4 °C. Then cells were washed twice before flow cytometry analysis using an Accuri C6 Plus (BD Biosciences). Data were analyzed using FlowJo software.

Example 6: Murine anti-CD25 dimerization is required for integrin activation. To assess whether a monovalent non-signaling version of PC61 retained the stimulating integrin activation ability, a single-chain fragment variable (scFv) version of rat-PC61 was expressed. The single-chain fragment variable (scFv) version of rat-PC61 was obtained from Dr. Mark D. Mannie (Wilkinson et al., 2017). Unlike the intact rat-PC61, PC61-scFv was not able to activate integrin on Tregs. Although this PC61-scFv protein has the same binding specificity compared with the rat-PC61, as it could compete with the intact rat-PC61 for integrin activation.

Figure 6A:
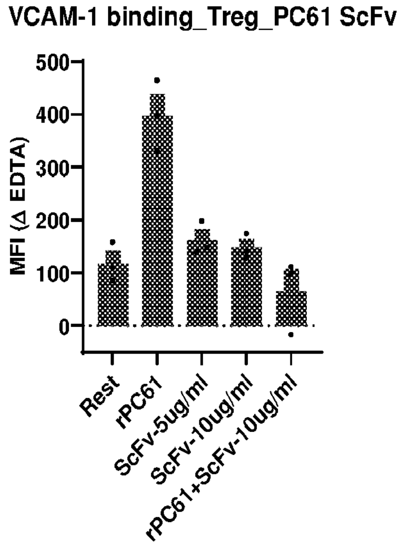
FIGS. 6A-6B show that Murine anti-CD25 dimerization is required for integrin activation.
Figure 6B:
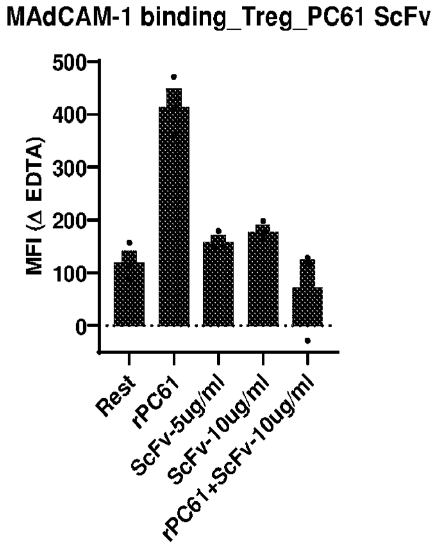

Specifically, FIGS. 6A-6B show binding of soluble VCAM-1 or MAdCAM-1 to GFP+ Tregs isolated from Foxp3GFP mice in the presence of rat-PC61 (5 ug/ml), PC61-scFv (5 ug/ml or 10 ug/ml) and rat-PC61 (5 ug/ml) plus PC61-scFv (5 ug/ml or 10 ug/ml). Data represent mean±SEM. Two-tailed t-test. ***P<0.001.

The PC61-scFv stably expressed HEK293F cells were kindly provided by Dr. Mark D. Mannie (Wilkinson et al., 2017). Briefly, the PC61-scFv gene encoded (from N-terminus to C-terminus) the rat serum albumin signal peptide, a poly-histidine affinity purification tag, the PC61 variable light chain domain, a $(Glycine_4Serine_1)_4$ linker, and the PC61 variable heavy chain domain. The PC61 VL and VH domain sequences were described previously (Huss et al., 2016). The PC61scFv gene sequence was cloned into the pIRES AcGFP1 expression vector (Clontech) and used to stably transfect HEK293F cells. PC61-scFv was purified using a column loaded with Ni-NTA resin, and purity was measured using SDS-PAGE. PC61scFv specificity and activity was validated by inhibition of IL-2-dependent proliferation of an IL-2-dependent cell line.

Splenic lymphocytes isolated from Foxp3$^{GFP}$ mice were washed and resuspended in HBSS containing 0.1% BSA and 1 mM $Ca^{2+}/Mg^{2+}$, prior to incubation with integrin ligands for 30 min at 37 °C in the presence of rat-PC61 (5 ug/ml, Bioxcell), PC61-scFv (5 ug/ml or 10 ug/ml) and rat-PC61 (5 ug/ml) plus PC61-scFv (10 ug/ml). Cells were then incubated with AlexFluor647-conjugated anti-human IgG (1:200) for 30 min at 4 °C. Then cells were washed twice before flow cytometry analysis using an Accuri C6 Plus (BD Biosciences). Data were analyzed using FlowJo software.

Figure 7A:
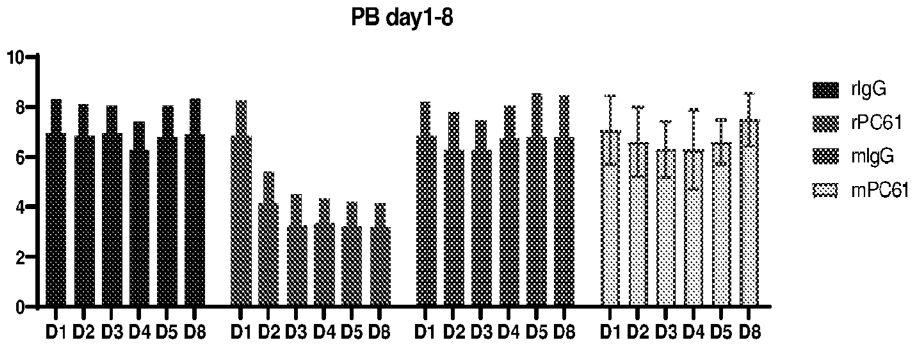
FIGS. 7A-7E show engineered murinized anti-CD25 (D265A) (mPC61) does not affect Tregs abundance in vivo, whereas, as is known, the parent Rat antibody (rPC61) does so.
Figures 7B, 7C, 7D, 7E:
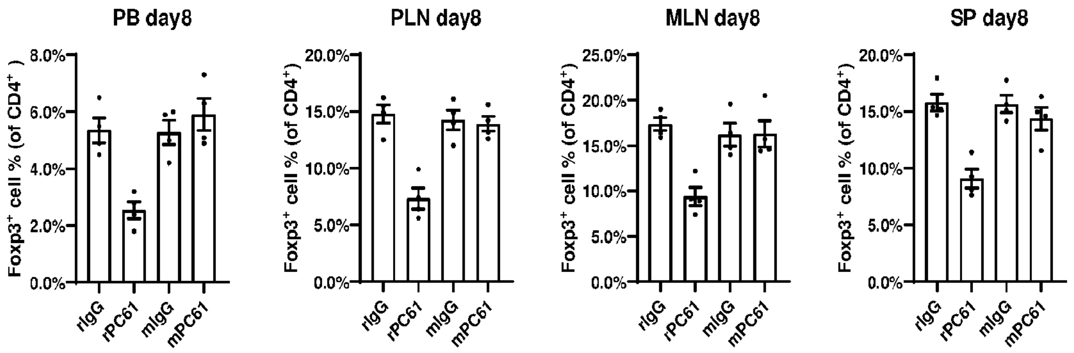

Example 7: Rat-PC61 is known as a Tregs depletion antibody. Murinized anti-CD25 doesn't affect Tregs abundance in vivo. The previous study revealed the depletion of Tregs by rat-PC61 was mediated by FcγRIII$^{+}$ phagocytes. Rat-PC61 targets on the Tregs, followed by the FcγRIII+ phagocytes recognizing the rat-IgG1 and clearing all the Tregs (Setiady et al., 2010). Next, whether murine-PC61 would be removed by phagocytes in the mouse, which has a D265A mutation on the mouse IgG1 heavy chain to avoid mouse IgG1 binding to mouse Fc receptors was tested (Bournazos et al., 2014; Clynes et al., 2000). Consistent with previous reports (Setiady et al., 2010), injection of rat-PC61 had a profound effect on the percentage of Tregs. In peripheral blood (FIG. 7A), $CD4^{+}Foxp3^{+}$ Tregs decreased significantly from about 6.83% to 4.15% just 1 day after rat-PC61 injection. The Tregs depletion reached its peak (3.13%) on day 8 (FIG. 7A). At the peak of Tregs depletion, around half of Tregs disappeared from lymph nodes and spleen (FIGS. 7B-7E). In contrast to rat-PC61, the murine-PC61 did not affect the Tregs percent in CD4+ cells in peripheral blood, lymph nodes and spleen (FIGS. 7A-7B).

Figure 8A:
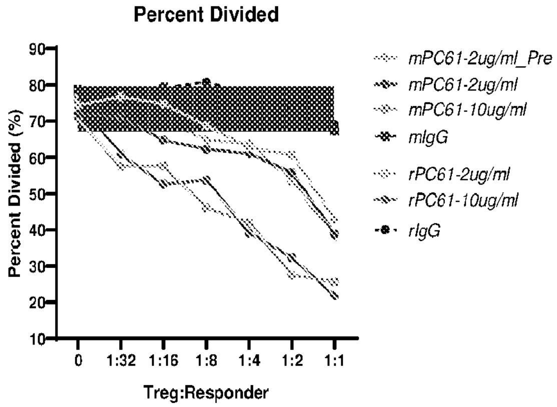
FIGS. 8A-8D show that both rat PC61 (rPC61) or murinized PC61 (mPC61) equally enhance the suppressive function of Tregs.
Figure 8B:
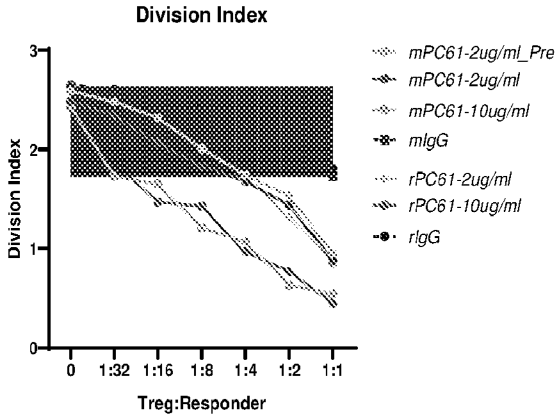
Figure 8C:
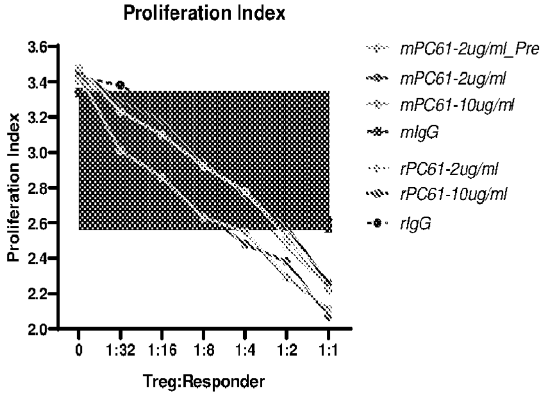
Figure 8D:
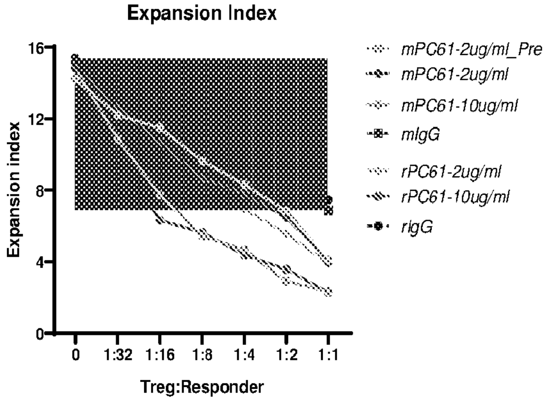

Specifically, in FIGS. 7A-7E, Foxp3$^{GFP}$ mice were intravenously injected with rat-PC61, rat-rIgG, murine-PC61 and murine-IgG (day 0, 200 ug/mouse) and the Treg levels (percentage of Foxp3+ cells in total CD4+ T cells) were determined in the peripheral blood (FIG. 7A), lymph nodes and spleen (FIG. 8B) on day 8. Data are representative of two experiments. Each symbol represents one mouse. Data represent mean±SEM. Two-way ANOVA with Bonferroni post test. ***P<0.001.

Foxp3$^{GFP}$ mice were injected i.v. with rat-PC61, rat-rIgG, murine-PC61 and murine-IgG (200 ug/mouse) at day 0. Peripheral blood, lymph nodes and spleen were collected and analyzed by Accuri C6 Plus (BD Biosciences) for CD4 and Foxp3$^{GFP}$ expression. CD4 was detected using an AlexFluor647-conjugated anti-CD4 mAb (clone GK15). Data were analyzed using FlowJo software.

Example 8: Rat and murinized anti-CD25 stimulate regulator T cell suppressive function. The effect of rat PC61 (rPC61) or murinized PC61 (mPC61) on the function of rergulatory Tcells (Treg). Depicted in FIGS. 8A-8D are four different measures of the growth of stimulated T cells (Responder) in the presence of the indicated ratio of added Tregs. The negative slopes indicate that in the presence of Tregs growth is reduced and either PC61 or mPC61 enhance the suppressive activity of Tregs compared to either rat or mouse IgG. Pre-incubation of Tregs with mPC61 followed by washing of unbound antibody (2 ug/ml mPC61-Pre)had the same effect as addition of mPC61 to the mix of Tregs and responders. Note: IgG controls were identical to those in the absence of added IgG and neither rPC61 or mPC61 had any effect in the absence of Tregs (not shown).

$CD4^+CD25^-$ T cells (Responder cells) were isolated from spleens of C57BL/6 (CD45.1) WT mice by magnetic separation using the $CD4^+$ T cell negative isolation kit (Biolegend); a biotin-conjugated anti-CD25 (PC61; BioLegend) Ab was included to deplete $T_{regs}$ cells. $YFP^+$ $T_{regs}$ were sorted with a FACSAria 2 (BD Biosciences). Responder cells were labelled with CFSE and cocultured with $T_{regs}$ cells (8:1, 4:1, 2:1 and 1:1 ratios) in the presence of 5 μg/ml immobilized antibodies against CD3 (2C11) and CD28 (37.51), and IL-2 for 4 days at 37 °C and the indicated concentration of added anti-CD25 antibodies or IgG controls. Growth parameters were calculated by FlowJo v10 from the dilution of CFSE in the responder cells.

REFERENCES

1. Bournazos, S., Klein, F., Pietzsch, J., Seaman, M. S., Nussenzweig, M. C., and Ravetch, J. V. (2014). Broadly neutralizing anti-HIV-1 antibodies require Fc effector functions for in vivo activity. Cell 158, 1243-1253.
2. Boyman, O., and Sprent, J. (2012). The role of interleukin-2 during homeostasis and activation of the immune system. Nat Rev Immunol 12, 180-190.
3. Clynes, R. A., Towers, T. L., Presta, L. G., and Ravetch, J. V. (2000). Inhibitory Fc receptors modulate in vivo cytotoxicity against tumor targets. Nature medicine 6, 443-446.
4. Chu et al., WO2014145907A1. Targeting T Cells with Heterodimeric Proteins.
5. Huss, D. J., Pellerin, A. F., Collette, B. P., Kannan, A. K., Peng, L., Datta, A., Wipke, B. T., and Fontenot, J. D. (2016). Anti-CD25 monoclonal antibody Fc variants differentially impact regulatory T cells and immune homeostasis Immunology 148, 276-286.
6. Kang and Jung Experimental & Molecular Medicine (2019) 51:138 https://doi.org/10.1038/s12276-019-0345-9.
7. Klann, J. E., Remedios, K. A., Kim, S. H., Metz, P. J., Lopez, J., Mack, L. A., Zheng, Y., Ginsberg, M. H., Petrich, B. G., and Chang, J. T. (2017). Talin Plays a Critical Role in the Maintenance of the Regulatory T Cell Pool. J. Immunol. 198, 4639-4651.
8. Klann, J. E., Kim, S. H., Remedios, K. A., He, Z., Metz, P. J., Lopez, J., Tysl, T., Olvera, J. G., Ablack, J. N., Cantor, J. M., et al. (2018). Integrin Activation Controls Regulatory T Cell-Mediated Peripheral Tolerance. J. Immunol. 200, 4012-4023.
9. Ku, C. C., Murakami, M., Sakamoto, A., Kappler, J., and Marrack, P. (2000). Control of homeostasis of CD8+ memory T cells by opposing cytokines. Science 288, 675-678.
10. Quezada et al., WO2017174331A1. Anti CD25 Fc Gamma Receptor Bispecific Antibodies for Tumor Specific Cell Depletion.
11. Setiady, Y. Y., Coccia, J. A., and Park, P. U. (2010). In vivo depletion of CD4+FOXP3+ Treg cells by the PC61 anti-CD25 monoclonal antibody is mediated by FcgammaRIII+phagocytes. Eur J Immunol 40, 780-786.
12. Wilkinson, D. S., Ghosh, D., Nickle, R. A., Moorman, C. D., and Mannie, M. D. (2017). Partial CD25 Antagonism Enables Dominance of Antigen-Inducible CD25(high) FOXP3(+) Regulatory T Cells As a Basis for a Regulatory T Cell-Based Adoptive Immunotherapy. Frontiers in immunology 8, 1782.

What is claimed is:

1. A method of treating an autoimmune disease or transplant rejection in a subject comprising administering to the subject a PC61 antibody of SEQ ID NO: 1 and SEQ ID NO: 2, wherein the PC61 antibody comprises a mutated Fc region comprising a D265A mutation.

2. The method of claim 1, wherein the autoimmune disease is systemic lupus erythematosus, multiple sclerosis, rheumatoid arthritis, chronic inflammation, or inflammatory bowel disease.

3. The method of claim 1, wherein the transplant rejection is due to pancreatic islet, heart, kidney, liver, lung, intestine, cornea, bone marrow, or connective tissue, transplantation or vascularized composite allografts.

4. A method of stimulating regulatory T cells (Tregs) in a subject, comprising administering to the subject a PC61 antibody of SEQ ID NO: 1 and SEQ ID NO: 2, wherein the PC61 antibody comprises a mutated Fc region comprising a D265A mutation.

* * * * *